United States Patent
Bertoni

(10) Patent No.: US 8,911,420 B2
(45) Date of Patent: Dec. 16, 2014

(54) DEVICE FOR THE CONTAINMENT OF PLATELET CONCENTRATES

(75) Inventor: Marco Bertoni, Modena (IT)

(73) Assignee: Biomed Device S.R.L., Reggello (FI) (IT)

( * ) Notice: Subject to any disclaimer, the term of this patent is extended or adjusted under 35 U.S.C. 154(b) by 86 days.

(21) Appl. No.: 13/574,299

(22) PCT Filed: Jan. 20, 2011

(86) PCT No.: PCT/IB2011/000079
§ 371 (c)(1),
(2), (4) Date: Jul. 20, 2012

(87) PCT Pub. No.: WO2011/089508
PCT Pub. Date: Jul. 28, 2011

(65) Prior Publication Data
US 2012/0292215 A1    Nov. 22, 2012

(30) Foreign Application Priority Data

Jan. 22, 2010 (IT) .............................. MO2010A0008

(51) Int. Cl.
| | | |
|---|---|---|
| *A61B 19/00* | (2006.01) | |
| *A61J 1/14* | (2006.01) | |
| *A61J 1/18* | (2006.01) | |
| *A61M 39/20* | (2006.01) | |
| *A61J 1/10* | (2006.01) | |
| *A61J 1/20* | (2006.01) | |

(52) U.S. Cl.
CPC .............. *A61J 1/1412* (2013.01); *A61J 1/1475* (2013.01); *A61J 1/18* (2013.01); *A61M 39/20* (2013.01); *A61J 1/10* (2013.01); *A61J 2001/1487* (2013.01); *A61J 2001/2027* (2013.01)
USPC ......................................... 604/403; 604/416

(58) Field of Classification Search
CPC ............................ F16K 3/0281; B65D 47/068
USPC .................................................. 604/403, 416
See application file for complete search history.

(56) References Cited

U.S. PATENT DOCUMENTS 2,279,834 A * 4/1942 McGee .......................... 251/342
3,800,799 A * 4/1974 McWhorter ................... 251/342
(Continued)

FOREIGN PATENT DOCUMENTS

DE          20203154      5/2002
DE        202009001068    4/2009
(Continued)

OTHER PUBLICATIONS

International Search Report dated Jun. 6, 2011, in corresponding PCT application.

*Primary Examiner* — Leslie Deak
(74) *Attorney, Agent, or Firm* — Young & Thompson

(57) ABSTRACT

A device (1) for the containment of platelet concentrates includes at least a bag (2) defining at least a containment chamber (3) having at least a mouth (4) for the entry of a platelet concentrate and at least a connection element for connection to an infusion line associated with the bag in correspondence to the mouth; the connection element includes a first and a second portion (5a, 5b) integrally associated together and includes at least a constantly open duct (6), passing through the first and the second portion and communicating with the chamber, where the first portion is associable with the infusion line and the second portion is associated with the bag in correspondence to the mouth, the first portion being separable from the second portion in such a way to interrupt the duct and define an opening (8) accessible from outside and including closing element (9) of the opening.

13 Claims, 1 Drawing Sheet

(56) References Cited

U.S. PATENT DOCUMENTS 4,306,705 A * 12/1981 Svensson .................. 251/149.9
4,397,442 A    8/1983 Larkin
6,533,759 B1 *  3/2003 Watson et al. ........... 604/167.02

FOREIGN PATENT DOCUMENTS

| GB | 2060399 | 5/1981 |
|----|---------|--------|
| WO | 2010085990 | 8/2010 |

* cited by examiner

DEVICE FOR THE CONTAINMENT OF PLATELET CONCENTRATES

TECHNICAL FIELD

The present invention relates to a device for the containment of platelet concentrates.

BACKGROUND ART

It is known that some types of lesions, such as corneal lesions or chronic ulcerative lesions, are considerably difficult to heal and, for this reason, not only result in continuous discomfort for the patients but also in high health costs.

Some modern health care methods envisage the use of platelet preparations, such as platelet concentrates or platelet gels, in order to treat the aforementioned lesions.

Platelet concentrate, also known as PRP (Plasma Rich in Platelets), is obtained by centrifuging a blood sample, while platelet gel, autologous or homologous, is generally obtained by adding activating substances such as thrombin and batroxobin, to a platelet concentrate. The platelet gel preparation can be made both before and at the time of use, by mixing the suitably prepared platelet concentrate with the aforementioned activating substances.

These platelet preparations contain numerous and important growth factors that stimulate the fundamental biological mechanisms for tissue repair and regeneration.

Generally, to treat corneal lesions, the platelet concentrate is used fresh and/or frozen, while chronic ulcerative lesions and, generally speaking, tissue regeneration are treated with platelet gel.

More in particular, the method used to date for the preparation of samples of platelet concentrate to be used as collyrium envisages filling a duct (dialysis intravenous line) made of plastic material and closing such duct, e.g. by sealing, in correspondence to a plurality of areas arranged in succession the one to the other and separated the one from the other, in such a way as to form a plurality of closed units.

These units are then opened, before being used, by cutting one of their respective extremities, e.g., using a pair of scissors, in such a way as to make their contents available for use.

The units of platelet concentrate can contain a single, daily or weekly dose, and their contents must be preserved at a temperature of around −40° C. before use and at around +4° C. for the first and the subsequent therapeutic uses (in the case of daily or weekly doses).

Generally speaking, in particular in the case of patients who are medicated at home, the open units of platelet concentrate are kept inside the domestic refrigerator which also contains food products.

These units, containing platelet concentrates made using the method of known type described above, have a number of drawbacks.

More in particular, the units of known type are not easy and safe to use and do not allow complying with the hygienic-health requirements of applicable laws and those of certification institutes for hemoderivatives.

In fact, opening these units with a pair of scissors or the like results in residues of organic material contained in the relative unit remaining on the cutting area of such scissors, with the consequent risk of contaminating the contents of the other units subsequently cut using the same pair of scissors.

This obviously creates the risk of the platelet content of the units cut by means of a pair of scissors already previously used being polluted by the residues remaining on the scissors themselves, thus compromising its therapeutic properties and above all considerably increasing the risk of secondary infections being caused in patients who are already immunodepressed and on an already compromised organ.

Another drawback of known units for the containment of platelet concentrate consists in the fact that, once opened, they do not allow the safe storage of their contents, which should instead be stored in an environment that is as sterile as possible.

In fact, as described above, the units containing daily or weekly doses of platelet concentrate are then generally stored inside normal domestic refrigerators, where they could be contaminated (including on the outside) by bacteria and microorganisms present on food products (eggs, dressed-pork products, vegetables . . . ) contained therein and by the bacterial flora, fauna and fungi normally present inside said environment.

More in detail, the containment units of known type, once opened, remain accessible from the outside, and consequently their contents could be contaminated by external agents.

Another drawback still of the containment units of known type consists in the fact that they do not make it possible to check the dosage of the platelet concentrate to be used.

Two known connection devices are described by DE 20203154 and by U.S. Pat. No. 4,397,442.

DE 20203154 describes a connection element for connecting a bag to an infusion line. This connection element comprises a main body, inside which is defined a flow duct for a liquid, closed at one extremity by a closing element removable by tearing off. The opposite extremity of such main body is obstructed by a cap, removable to allow access from outside.

More in particular, to use the connection element subject of DE 20203154, the closing element must first of all be removed so as to open the flow duct and be able to connect the relative extremity of the main body to a containment bag, and remove the cap from the opposite extremity to allow the treated liquid to flow off.

Once the closing element is removed from the main body, it is no longer possible to reposition it on the latter, while the cap fitted at the opposite extremity of the main body has the sole purpose of obstructing the flow duct and must necessarily be removed to allow the flow of the treated liquid and therefore the filling of the relative bag.

The connection device described by DE 20203145 does not appear very easy to use inasmuch as it necessarily requires the removal of the closing element and of the cap from the main body before use and, once the relative bag has been filled, requires the removal of the infusion line from the main body and the closing of the flow duct by means of the cap itself. During bag filling, the closing cap is therefore separate and released with respect to the connection device, with the risk of its being lost or in any case not easily identifiable in case of need.

Furthermore, the realisation of the connection device subject of DE 20203145 requires the separate realisation of the main body and of the closing cap, for example using two separate moulds, and this means that manufacture is complicated and costly.

U.S. Pat. No. 4,397,442 describes a valve device suitable for allowing/preventing the flow of a liquid through it and associable with a containment bag.

More in particular, this valve device comprises a fixed portion and a mobile portion.

The fixed portion and the mobile portion are both tubular shaped and define a flow duct for the transit of the treated liquid. The fixed portion also has a protuberance suitable for being inserted inside the mobile portion to obstruct the liquid flow duct.

The mobile portion associated integral with the fixed portion, in turn comprises a flexible flange suitable for permitting the reciprocal movement of such portions.

The movement of the mobile portion with respect to the fixed portion makes it possible to modify the section of liquid flow duct, choking the flow of treated liquid. The mobile portion thus moves between two extreme positions, one closing the flow duct and one opening the flow duct to maximum extent, passing through a plurality of intermediate positions, each of which corresponds to a different section of the duct itself and, therefore, to a different liquid flow rate.

This valve device, as such, does not allow tilling a container easily and quickly because the mobile part must be manually moved to an open position and kept this position during the entire procedure to allow the flow of the liquid.

Furthermore, this valve device does not ensure either the seal or the safe preservation of the liquid once the bag associated with the device itself has been filled, inasmuch as the accidental movement of the mobile portion can cause the opening of the flow duct and, therefore, the escape of the liquid. The use of a removable safety cap further complicates the realisation and use of such valve device, inasmuch as it requires the control of a further component separate and independent of the others.

DESCRIPTION OF THE INVENTION

The main aim of the present invention is to provide a device for the containment of platelet concentrates which is practical and safe to use.

Inside such aim, one object of the present invention is to provide a device for the containment of platelet concentrates that allows filling a relative bag in an easy and fast way, without the need of moving or removing any component.

Another object of the present invention is to provide a device that allows easily filling the relative bag and which, at the same time, allows protecting its contents from external contamination factors also once it has been opened to dispense its contents.

Another object of the device for the containment of platelet concentrates according to the invention is to allow, following its opening, the control of the dosing of the platelet concentrate itself.

Another object of the present invention is to provide a device for preparing units for the containment of platelet preparations which complies with the hygienic sanitary requirements laid down by applicable laws and which is, besides easy to use and safe, also easy and inexpensive to make.

Another object of the present invention is to provide a device for the containment of platelet concentrates which allows overcoming the mentioned drawbacks of the state of the art within the ambit of a simple, rational, easy and effective to use as well as low cost solution.

The above objects are achieved by the present device for the containment of platelet concentrates comprising at least a bag which defines at least a containment chamber having at least a mouth for the entry of a platelet concentrate and at least a connection element for the connection to an infusion line associated with said bag in correspondence to said mouth, characterised by the fact that said connection element comprises a first and a second portion integrally associated together and comprises at least a constantly open duct, passing through said first and said second portion and communicating with said chamber, where said first portion is associable with said infusion line and said second portion is associated with said bag in correspondence to said mouth, said first portion being separable from said second portion in such a way to interrupt said duct and define an opening accessible from outside and comprising closing means of said opening.

BRIEF DESCRIPTION OF THE DRAWINGS

Other characteristics and advantages of the present invention will become more evident from the description of a preferred, but not sole, embodiment of a device for the containment of platelet preparations, illustrated purely as an example but not limited to the annexed drawings in which.

EMBODIMENTS OF THE INVENTION

Figure 1:
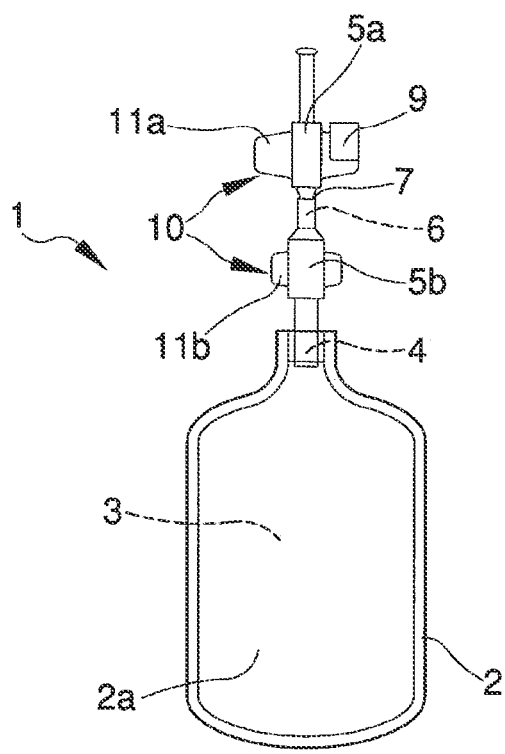
FIG. 1 is a side raised view of a device for the containment of platelet concentrates according to the invention.
Figure 2:
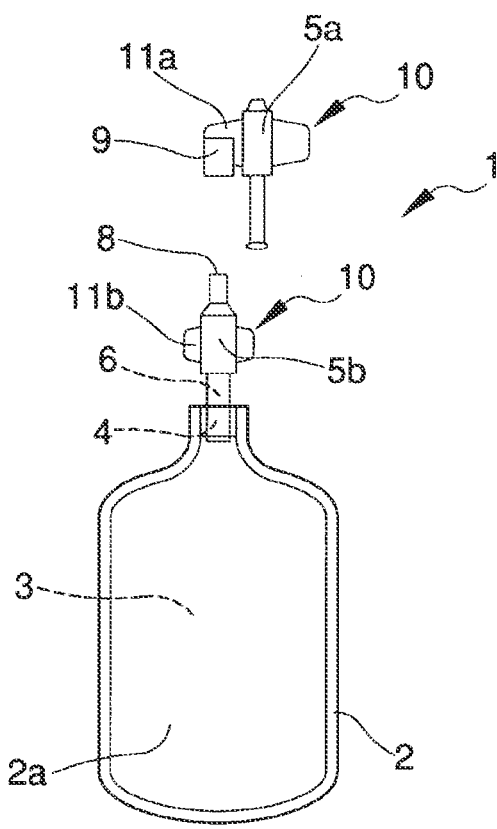
FIG. 2 is a side raised view of the device for the containment of FIG. 1 with the first portion of the connection element detached from the relative second portion.
Figure 3:
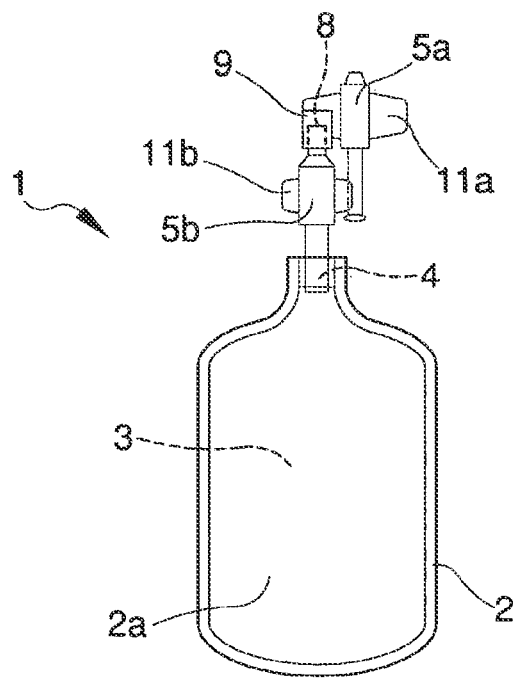
FIG. 3 is a side raised view of the device for the containment of FIG. 1 with the first portion of the connection element fitted on the relative second portion.
Figure 4:
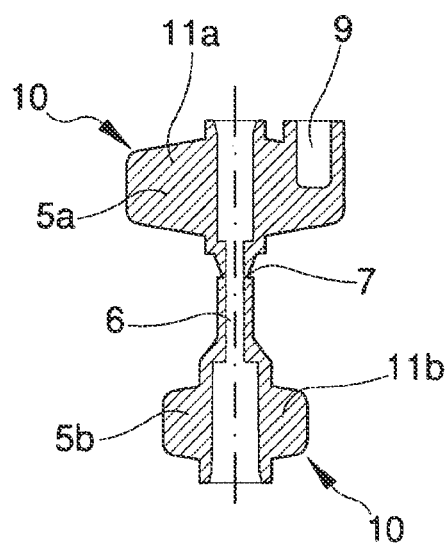
FIG. 4 is a longitudinal section of the connection element of the device for the containment of FIG. 1.

With particular reference to such figures, globally indicated by 1 is a device for the containment of platelet concentrates.

The device 1 comprises at least a bag 2 defining at least a containment chamber 3 for containing a platelet concentrate. The chamber 3 has at least a mouth 4 for the entry of the platelet concentrate.

More in particular, the bag 2 comprises two containment walls 2a associated with one another along the relevant perimeter edges to define the chamber 3.

The containment device 1 comprises at least a connection element 5a, 5b associable with an infusion line not represented in the figures from 1 to 4 and associated with the bag 2 in correspondence to the mouth 4.

According to the invention, the connection element 5a, 5b comprises a first and a second portion 5a and 5b associated the one with the other and comprises at least a flow duct 6 for the platelet concentrate. The duct 6 is constantly open, passes through the first and the second portion 5a, 5b and communicates with the chamber 3 through the mouth 4. The first and the second portion 5a and 5b, associated with the infusion line and with the bag 2 respectively, are then crossed in a through way by the duct 6.

More in particular, the second portion 5b is associated with the bag 2 by means of the mouth 4.

Suitably, the first and the second portions 5a and 5b are fixed the one with respect to the other.

Furthermore, the duct 6 has a fixed section, i.e., not adjustable, and therefore the flow of platelet concentrate that crosses it is substantially constant.

According to the invention, furthermore, the first portion 5 is removable from the second portion 5b, so as to interrupt the duct 6 and define an opening 8 accessible from outside, and comprises closing means 9 for closing the opening 8.

The opening 8 corresponds, during use, to the exit opening of the substance contained inside the chamber 3.

Advantageously, the first portion 5a is removable by tearing off from the second portion 5b.

More in detail, the joining area 7 of the first and the second portions 5a and 5b is weakened to facilitate the separation of the first portion 5a from the second portion 5b.

Preferably, the joining area 7 has a predefined breakage line.

Advantageously, the closing means 9 can be fitted on the second portion 5b.

More in particular, the closing means 9 comprise a blind recess which can be fitted on the extremity section of the second portion 5b defining the opening 8.

The first portion 5a is therefore suitable for covering the opening 8 again after its removal.

Preferably, the connection element 5a, 5b comprises separation means 10 for separating the two portions 5a and 5b.

In the preferred embodiment represented in the figures from 1 to 4, the separation means 10 comprise at least two pairs of grip fins 11a and 11b arranged on opposite sides with respect to the joining area 7.

More in particular, the separation means 10 comprise at least a first pair of grip fins 11a associated with the first portion 5a and at least a second pair of grip fins 11b associated with the second portion 5b.

The first and the second pair of grip fins 11a and 11b can be gripped by an operator and are meant to turn in the opposite direction the one to the other so as to stress the material making up the connection element 5a, 5b and substantially tear the first portion 5a from the second portion 5b.

Advantageously, the blind recess 9, suitable for covering the opening 8 to isolate the flow duct 6 from outside, is defined in correspondence to a fin of the first pair of grip fins 11a.

The operation of the present invention is the following.

The operation of the containment device 1 appears immediately understandable by a technician in the sector.

During the filling of the chamber 3, i.e., with the first and the second portions 5a and 5b associated integral and fixed the one with respect to the other, the duct 6 is constantly open and the platelet concentrate flows off through it at a constant rate.

More in detail, after suitably filling the chamber 3 by introducing the platelet concentrate inside it through the duct 6, this flow duct is closed, normally by sealing, upstream of the first portion 5a with respect to the direction of entry of the platelet concentrate into the chamber itself.

The chamber 3, which can be filled with a single, daily or weekly dose of platelet concentrate, is thus isolated from the outside.

To be able to use the contents of the containment device 1, the first portion 5a will have to be removed from the second portion 5b. This is done, as stated above, by turning the first and the second grip fins 11a and 11b in the opposite direction the one to the other so as to break the material making them up in correspondence to their joining area 7.

The opening of the containment device 1 does not therefore require the use of cutting means.

Following the removal of the first portion 5a, the end section of the second portion 5b is therefore accessible from outside and defines the opening 8 through which the platelet preparation contained in the chamber 3 can be made to come out.

After using the platelet preparation for therapeutic purposes, in particular in the case of bags 2 sized to contain a single, daily or weekly dose, the operator closes the opening 8 by applying onto this the first portion 5a previously removed and therefore released with respect to the second portion 5b.

More in detail, the operator fits the blind recess 9 defined on a fin of the first pair of grip fins 11a on the extremity section of the second portion 5b comprising the opening 8.

The first portion 5a now therefore acts as a cap for the second portion 5b and the opening 8 is therefore isolated from the outside and protected against contamination agents.

Making a new dose of the platelet preparation simply requires lifting the first portion 5a so as to again uncover the opening 8.

It has in fact been ascertained how the described invention achieves the proposed objects and in particular the fact is underlined that the containment device according to the invention allows filling a bag in an easy and practical way and at the same time safely preserving its contents, even after the relevant bag has been opened.

In fact, the connection element of the device in question, by defining a normally open duct, permits fast and easy filling of the relevant bag and this same connection element, following the removal of the first portion from the second portion, allows easily opening/closing the duct itself without the use of further elements.

Again, the device according to the invention is easy and inexpensive to make inasmuch as made in a single piece, with a consequent saving of material and equipment.

Furthermore, the presence of a pair of fins on both the portions making up the connection element allows the easy and practical separation of same.

The invention claimed is:

1. Device (1) for the containment of platelet concentrates, comprising:
    at least a bag (2) which defines at least a containment chamber (3) having at least a mouth (4) for the entry of a platelet concentrate; and
    at least a connection element (5a, 5b) for the connection to an infusion line associated with said bag (2) in correspondence to said mouth (4),
    wherein said connection element (5a, 5b) is a single piece comprised of a first portion (5a) fixed to a second portion (5b) at a joining area (7) and comprises at least a constantly open duct (6), passing through said first and said second portions (5a, 5b) and communicating with said chamber (3), said joining area (7) adapted for separating the first portion (5a) from the second portion (5b) by tearing the first portion (5a) off from the second portion (5b),
    where said first portion (5a) is associable with said infusion line and said second portion (5b) is associated with said bag (2) in correspondence to said mouth (4),
    said first portion (5a) i) being separable from said second portion (5b) at the joining area in such a way to interrupt said duct (6) and define an opening (8) at said second portion (5b) accessible from outside, and ii) comprising closing means (9) that fits on said opening (8) at said second portion (5b),
    wherein the opening (8) corresponds, during use, to an exit opening of the substance contained inside the chamber (3).

2. Device (1) according to claim 1, wherein said closing means (9) comprise a blind recess which can be fitted on the extremity section of said second portion (5b) defining said opening (8).

3. Device (1) according to claim 1, wherein said duct (6) has a fixed section.

4. Device (1) according to claim 1, wherein said connection element (5a, 5b) comprises separation means (10) for separating said portions (5a, 5b).

5. Device (1) according to claim 4, wherein said separation means (10) comprise at least two pairs of grip fins (11a, 11b) arranged on opposite sides with respect to said joining area (7).

6. Device (1) according to claim 5, wherein said separation means (10) comprise at least a first pair of grip fins (11a) associated with said first portion (5a) and at least a second pair of grip fins (11b) associated with said second portion (5b).

7. Device (1) according to claim 6, wherein said closing means (9) are defined in correspondence to said first pair of grip fins (11a).

8. Device (1) according to claim 1, wherein,
the joining area (7) comprises a predefined breakage line that allows the first portion (5a) to be removed from the second portion (5b) by tearing the first portion (5a) off from the second portion (5b) at the breakage line, the breakage line being an area of locally reduced diameter relative to immediately adjacent diameters of the first and second portions (5a, 5b).

9. Device (1) according to claim 8, wherein,
the device is made in a single piece.

10. Device (1) according to claim 1, wherein,
said joining area (7) comprises a predefined breakage line that allows the first portion (5a) to be removed from the second portion (5b) by tearing the first portion (5a) off from the second portion (5b) at the breakage line, the breakage line is an area of locally reduced diameter relative to immediately adjacent diameters of the first and second portions (5a, 5b),
each of said first and portions (5a, 5b) include a pair of grip fins (11a, 11b) that are gripable by an operator to turn the first and second portions (5a, 5b) in opposite directions so as to stress a reduced-diameter breakage line located between the first and second portions (5a, 5b) and tear the first portion (5a) off from the second portion (5b) at the breakage line, and
one fin of the pair of fins associated with the first portion (5a) comprises the closing means (9).

11. Device (1) for the containment of platelet concentrates, comprising:
a bag (2) with two containment walls (2a) associated with one another along a perimeter edge of the bag, the two walls defining a containment chamber (3) having a mouth (4) for entry of a platelet concentrate,
a connection element (5a, 5b) that connects to an infusion line associated with said bag (2) in correspondence to said mouth (4),
wherein said connection element (5a, 5b) comprises i) a first portion (5a) and a second portion (5b) integrally associated together and ii) a constantly open duct (6), passing through said first and said second portions (5a, 5b) and communicating with said chamber (3) by said duct (6) extending through said mouth (4) into the containment chamber (3),
wherein said first portion (5a) is associable with said infusion line and said second portion (5b) is associated with said bag (2) in correspondence to said mouth (4),
wherein said first portion (5a) is removable from said second portion (5b) in such a way to interrupt said duct (6) and define an opening (8) accessible from outside and that allows a contents of the containment chamber (3) to outflow via said mouth (4) and said opening (8), and
wherein said first portion (5a) comprises a closing means (9) defining a cap that closes said opening (8) when fitted onto said opening (8), wherein,
said connection element (5a, 5b) comprises a joining area (7) with a predefined breakage line that allows the first portion (5a) to be removed from the second portion (5b) by tearing the first portion (5a) off from the second portion (5b) at the breakage line, the breakage line being an area of locally reduced diameter relative to immediately adjacent diameters of the first and second portions (5a, 5b).

12. Device (1) according to claim 11, wherein,
the device is made in a single piece.

13. Device (1) for the containment of platelet concentrates, comprising:
a bag (2) with two containment walls (2a) associated with one another along a perimeter edge of the bag, the two walls defining a containment chamber (3) having a mouth (4) for entry of a platelet concentrate,
a connection element (5a, 5b) that connects to an infusion line associated with said bag (2) in correspondence to said mouth (4),
wherein said connection element (5a, 5b) comprises i) a first portion (5a) and a second portion (5b) integrally associated together and ii) a constantly open duct (6), passing through said first and said second portions (5a, 5b) and communicating with said chamber (3) by said duct (6) extending through said mouth (4) into the containment chamber (3),
wherein said first portion (5a) is associable with said infusion line and said second portion (5b) is associated with said bag (2) in correspondence to said mouth (4),
wherein said first portion (5a) is removable from said second portion (5b) in such a way to interrupt said duct (6) and define an opening (8) accessible from outside and that allows a contents of the containment chamber (3) to outflow via said mouth (4) and said opening (8), and
wherein said first portion (5a) comprises a closing means (9) defining a cap that closes said opening (8) when fitted onto said opening (8), wherein,
said connection element (5a, 5b) comprises a joining area (7) with a predefined breakage line that allows the first portion (5a) to be removed from the second portion (5b) by tearing the first portion (5a) off from the second portion (5b) at the breakage line, the breakage line being an area of locally reduced diameter relative to immediately adjacent diameters of the first and second portions (5a, 5b),
each of said first and portions (5a, 5b) define a respective flow passage and each include a pair of grip fins (11a, 11b) that are gripable by an operator to turn the first and second portions (5a, 5b) in opposite directions so as to stress the breakage line and tear the first portion (5a) off from the second portion (5b) at the breakage line, and
one fin of the pair of fins associated with the first portion (5a) comprises the closing means (9).

* * * * *